United States Patent [19]

McNeely

[11] 4,240,926

[45] Dec. 23, 1980

[54] STERILIZATION INDICATOR

[75] Inventor: Gerald W. McNeely, Arden, N.C.

[73] Assignee: Akzona Incorporated, Asheville, N.C.

[21] Appl. No.: 15,546

[22] Filed: Feb. 26, 1979

[51] Int. Cl.$^3$ .................. C09K 3/00; C01K 11/16; C01N 21/06; C01N 21/10; C01N 31/22; C09D 11/10

[52] U.S. Cl. .................. 252/408; 23/230 R; 73/335; 73/356; 106/14.5; 106/20; 106/21; 116/206; 116/207; 116/216

[58] Field of Search ............ 73/356, 73, 77, 335; 252/408; 116/206, 207, 216; 106/20, 21, 14.5; 23/230 R

[56] References Cited

U.S. PATENT DOCUMENTS

| | | | |
|---|---|---|---|
| 2,798,855 | 7/1957 | Hainsworth | 252/408 |
| 2,798,856 | 7/1957 | Hainsworth | 252/408 |
| 2,826,073 | 3/1958 | Huyck et al. | 73/356 |
| 3,093,242 | 6/1963 | Huyck et al. | 116/206 |
| 3,098,751 | 7/1963 | Huyck et al. | 252/408 |
| 3,386,807 | 6/1968 | Edenbaum | 73/356 |
| 3,627,469 | 12/1971 | Cheng | 252/408 |
| 3,684,737 | 8/1972 | Emich | 252/408 |
| 3,862,824 | 1/1975 | Chapman | 252/408 |
| 4,155,895 | 5/1979 | Rohowetz et al. | 106/21 |
| 4,179,397 | 12/1979 | Rohowetz et al. | 252/408 |

*Primary Examiner*—Teddy S. Gron
*Attorney, Agent, or Firm*—Robert H. Falk; Charles A. Wendel; Francis W. Young

[57] ABSTRACT

A novel composition is disclosed which is useful as a sterilization indicator that can distinguish clearly between the types of sterilization employed, e.g., that indicates whether sterilization was accomplished by steam or dry heat. The novel composition comprises (1) thiobarbituric acid and (2) at least one suitable reacting moiety being capable of reacting with said acid under temperature and humidity conditions of steam and dry heat sterilization to form a colored product. Suitable reacting moieties disclosed are (a) parabanic acid and (b) dimethyl oxalate and urea.

5 Claims, No Drawings

STERILIZATION INDICATOR

BACKGROUND OF THE INVENTION

1. Field of the Invention

This invention relates to compositions that change color in response to temperature and humidity. More particularly, the invention relates to compositions that can be used in conjuction with articles to be sterilized to indicate whether these articles have been exposed to sterilizing conditions and whether the sterilization was accomplished by steam or dry heat.

2. Description of the Prior Art, and Other Information

Compositions that change color with changes in temperature have been known since at least 1928 when Davis applied for his patent (issuing as U.S. Pat. No. 1,777,353), which discloses that when the reaction product of cobalt cyanate with a tertiary base is dissolved in a suitable solvent such as chloroform, benzene, alcohol, acetone, toluene, or xylene, the resulting solution has the property of changing color from clear pink to lilac to violet to deep blue with increasing temperature. Such a composition cannot be used as a sterilization indicator, however, since the color change probable reverses with decreasing temperature and thus does not record a pre-existing temperature condition (Davis does not state ipsis verbis that the color change is reversible, however, reversibility is implied in the discussion of equilibrium, and also by the fact that:

blue colored sol.+pyridine→pink color pink colored sol.→blue sol.;

a complex forms at room temperature but is unstable at elevated temperatures). Even if this defect were not present, such solutions would be of limited usefulness, since generally they boil at no more than about 135° C., a temperature very near ordinary sterilization temperatures (the boiling point depends upon the solvent and the color changing temperature depends upon the solvent and quantity of pyridine in solution). Further, these solutions show only changes in the hue of the deep blue color, and not the color itself, between 100° C. and 135° C., the ordinary temperature range for sterilization.

In 1958, Huyck and Romito (U.S. Pat. No. 2,826,073) mentioned, but did not describe, "thermosensitive indicating materials capable of undergoing color changes" for use in devices for indicating completion of sterilization processes. The following year Korpman described (U.S. Pat. No. 2,889,799) a pressure sensitive adhesive tape for packaging surgical articles which incorporates a composition that undergoes a color change upon exposure to conditions necessary for sterilization. The composition may be one of several specified heat modifiable organic dyes, or organic dye intermediates or derivatives. It may also be a metallic salt system, (a lead oxide and sulfur system being specified), one of certain pH indicator systems, or one of certain diazonium compound systems. These materials have several drawbacks, however. First, organic dyes, and particularly those used as pH indicators, are prone to degrade under the ambient conditions associated with sterilization, such as exposure to actinic radiation. See Emigh, infra, at col. 2, lines 43-50. The alternate use of systems involving heavy metal compounds is undesirable because of the high toxicity of many of these which would prove detrimental in many cases, e.g., where the sterilized articles are for use in medicine. Another drawback to the use of the materials of Korpman is the inability of these materials to indicate the type of sterilization employed, e.g., whether steam or dry heat sterilization is being employed. See col. 3, lines 9-25 of U.S. Pat. No. 2,889,799. Such information is improtant since some sterilization methods should not be used for certain articles. Arthur H. Brian et al, BACTERIOLOGY 79-82 (6th ed. 1972).

In 1972, Emigh disclosed (U.S. Pat. No. 3,684,737) heavy metal halide coating compositions for use in indicating sterilization by ethylene oxide, steam or dry heat. As mentioned above, however, the use of heavy metal salts, many of which are quite toxic, is undesirable in many cases. Another disadvantage of the Emigh composition is that it does not so distinctly differentiate among the types of sterilization employed as to be unambiguous.

In 1974, Chapman disclosed in U.S. Pat. No. 3,837,809 a sterilization indicator using a sulphite, such as sodium sulphite. However, it is useful only for steam sterilizations employing formaldehyde vapor, and has the drawback of producing caustic byproducts such as, in the case of sodium sulphite, sodium hydroxide.

In 1976, Augurt mentioned in U.S. Pat. No. 3,991,881 the simultaneous use of separate indicators for steam and ethylene oxide sterilization, but did not describe the materials used for either.

Of further interest are U.S. Pat. Nos. 3,969,264; 3,568,627; 4,063,878; 3,038,812; 3,430,491; 4,014,260; 3,901,148 and 4,006,686.

U.S. Pat. No. 3,969,264, issued to Davis, discloses the concept of encapsulating liquid crystals which are heat responsive. However, the patent states that the colors are dull because the encapsulating material is not sufficiently transparent, although a color change apparently is perceivable. It does state that another patent, U.S. Pat. No. 3,620,889, calls for the use of a clear plastic resin in combination with liquid crystals. However, in column 1, lines 25-28, the U.S. Pat. No. 3,964,264 states that microencapsulated materials can not be printed.

U.S. Pat. 3,038,812 discloses the use of microencapsulated temperature indicators which are attached to paper by dipping the paper into a slurry, including such microencapsulated materials.

U.S. Pat. No. 3,568,627 discloses a steam sterility indicator which utilizes an indicator bar and a standard bar. There is further provided indicator material which encompasses numerals to show that the entire indicator card has been sterilized. It is uncertain as to whether or not the numerals are actually part of the indicator itself.

SUMMARY OF THE INVENTION

An object of the present invention is to provide a new and improved sterilization indicator composition that does not degrade under ambient sterilization conditions, is relatively non-toxic (when compared to the use of inorganic salts having metals), and avoids the formation of caustic by-products.

Another object of this invention is to provide a sterilization indicator that clearly distinguishes between the types of sterilization employed and that indicates whether sterilization was accomplished by steam or dry heat.

Another object of this invention is that all the foregoing advantages be provided in a single indicator composition.

In accordance with this invention these and various other related objectives will become apparent from a detailed consideration of the remainder of this specification, and are achieved in a simple novel composition that will change to one color when exposed to steam sterilization but a distinctly different color when exposed to dry heat sterilization. The composition is advantageously used as an ink, which when applied to an article is barely visible.

BRIEF DESCRIPTION OF THE PREFERRED EMBODIMENTS

In general, the reacting organic compounds constituting the composition of this invention comprise (1) thiobarbituric acid, and (2) at least one suitable reacting moiety, said moiety being capable of reacting with said acid under temperature and humidity conditions of steam and dry heat sterilizations to form a colored product. In one embodiment, the product produced under temperature and humidity conditions of steam sterilization is distinctly different in color from the colored product under temperature and humidity conditions of dry heat sterilization.

The reacting organic compounds constituting the composition of this invention comprise a system which may preferably be either (1) parabanic acid and thiobarbituric acid, or (2) dimethyl oxalate, urea, and thiobarbituric acid.

Hence, one has a choice of two preferable suitable reacting moieties to combine with thiobarbituric acid: (a) parabanic acid or (b) a combination of dimethyl oxalate and urea. If either preferable moiety is used, the novel composition has an initial cream color. Under steam sterilization between 100° C. and 130° C., a reaction takes place in either of these systems after a short exposure time to produce an easily detectable wine-red colored product. The chemistry of these solid-body reactions is not known. Fritz Feigl, SPOT TESTS IN ORGANIC ANALYSIS 404,433 (Elseveier Publishing Co., Amsterdam, N.Y., 6th ed. 1960).

To use either preferable system most advantageously, it may be formulated as an ink by combining the reacting organic compounds of the system with a water insoluble polymeric binder and a volatile organic solvent that dissolves all or part of the components. Any particular order of blending the components is suitable. Any suitable water insoluble polymeric binder known to those in the art may be employed. One such binder is named "RESINOX RJ-101 TM " and is manufactured by The Monsanto Company, Trenton, Michigan 48183, and is a proprietary composition. Other suitable binders are ethyl celluose, vinyl resins (such as polyvinyl acetate) and acrylic resins. As to the suitable volatile organic solvent employed, one may use one or more of tetrahydrofuran (THF), acetone, or a low boiling alcohol such as methanol, ethanol, or isopropanol with either system.

The reacting organic compounds should be present in a two to one mol ratio if the parabanic acid moiety is employed (see Example I), and a 1 to 1 to 2 mol ratio if the dimethyl oxalate/urea moiety is chosen. The binder content recommended may range from about 15 to about 30% by weight of the total ink composition. The amount of solvent may range from about 30 to about 60 weight % of the total ink composition. Lower amounts of solvent may be employed under certain conditions, but at some point a slurry might result that would be difficult to print, and higher percentages could reduce the intensity of the final color. After being formulated, the ink may be applied to various articles by various encapsulation means known to those skilled in the art. When the inked articles are exposed to steam or dry heat sterilization at from about 100° C. to about 130° C., for from about 5 to about 15 minutes, the ink takes on a wine-red or golden yellow color respectively to record the sterilization.

The invention is illustrated in the following examples, which are not to be taken as limiting the scope of the invention as defined in the appended claims.

EXAMPLES

EXAMPLE 1.

A cream colored ink was formulated from the following chemcials:

| Thiobarbituric Acid | 2.88 gms. (4.0M) |
|---|---|
| Parabanic Acid | 1.14 gms. (2.0M) |
| Resinox RJ-101 | 2.20 gms. |
| Tetrahydrofuran (THF) | 4.95 ml. |

At room temperature the thiobarbituric acid was ground in a ball mill for several hours, then added to a stirring solution of parabanic acid and RESINOX RJ-101 TM in THF. The resulting slurry was used to print various words and numbers onto strips of paper tape. The resulting slurry or mixture was used to print the word "DATE" on short strips of tape (AUTOCLAVE TAPE TM , Stock No. PG13P by the Armak Company, Chicago, Ill.). The resulting slurry was poured onto an absorbent cloth pad or celluose sponge normally used by those in the printing art and then transferred from the pad to a strip of cream colored tape by means of a buffer stamp. For a given pad, stamp, and tape, the amount of slurry transferred depended upon the stamp pressure applied to both the pad and tape. Rubber stamps that had various words or numbers or combinations of words and numbers were used to print the slurry on the tape. After drying for a few minutes, the cream colored print was barely visible on the tapes. The printed tapes were exposed to steam at 120° C. for 15 minutes after which the print had turned to a wine-red color. Other samples of the same printed tape were exposed to dry heat at temperatures of 115° to 120° C. for 20 minutes and the print turned to a golden-yellow color.

EXAMPLE II

A cream colored ink was formulated from the following chemicals:

| Dimethyl Oxalate | 1.18 gms. |
|---|---|
| Urea | 0.60 gms. |
| Thiobarbituric Acid | 2.88 gms. |
| Resinox RJ-101 | 2.20 gms. |
| THF | 5.00 ml. |

The components were mixed and prepared in the same manner as Example I. The resulting slurry was used to print the word "DATE" on short strips of the tape, in the same manner as Example I. After drying for a few minutes, the cream colored print was barely visible on the tape. The printed tapes were exposed to steam at 120° C. for 15 minutes after which the print had turned to a wine-red color. Other samples of the same printed tape were exposed to dry heat at temperatures of 115 to 120° C. for 20 minutes and the print turned to a golden-yellow color.

I claim as my invention:

1. A composition capable of recording steam and dry heat sterilizations and capable of differentiating therebetween, comprising:
   (1) thiobarbituric acid and (2) parabanic acid, to form a colored product.

2. A composition capable of recording steam and dry heat sterilizations and capable of differentiating therebetween, comprising:
   (1) thiobarbituric acid and (2) a mixture of dimethyl oxalate and urea, to form a colored product.

3. An ink capable of changing color in response to temperature and humidity conditions of steam and dry heat sterilizations to record said sterilizations, comprising:
   (a) the compositions of claims 1 or 2;
   (b) at least one water insoluble polymeric binder; and
   (c) a volatile organic solvent.

4. An ink as in claim 3, wherein said at least one water insoluble polymeric binder is RESINOX RJ-101 TM.

5. An ink as in claim 3, wherein said volatile organic solvent is selected from the group consisting of tetrahydrofuran, acetone, and low boiling alcohols.

* * * * *